United States Patent [19]

Horai

[11] Patent Number: 6,057,926
[45] Date of Patent: May 2, 2000

[54] MAGNETIC DISK TESTING METHOD AND SURFACE DEFECT TESTING DEVICE

[75] Inventor: Izuo Horai, Odawara, Japan

[73] Assignee: Hitachi Electronics Engineering Co., Ltd., Tokyo, Japan

[21] Appl. No.: 09/102,559

[22] Filed: Jun. 23, 1998

[30] Foreign Application Priority Data

Jun. 25, 1997 [JP] Japan .................................. 9-184432
Sep. 7, 1997 [JP] Japan .................................. 9-199418

[51] Int. Cl.[7] ........................... G01N 21/32; G01N 21/86
[52] U.S. Cl. ...................... 356/430; 356/431; 356/237.2; 356/237.3
[58] Field of Search ........................ 364/468.17, 468.16; 382/145, 146; 356/237.2, 237.3, 237.4, 237.5, 352; 369/44.32, 58; 250/559.4

[56] References Cited

U.S. PATENT DOCUMENTS

| | | |
|---|---|---|
| 4,794,265 | 12/1988 | Quackenbos et al. . |
| 5,031,112 | 7/1991 | Sakai et al. .................... 356/237.4 |
| 5,423,111 | 6/1995 | Mori . |
| 5,625,193 | 4/1997 | Broude et al. .................... 250/372 |
| 5,646,415 | 7/1997 | Yanagisawa .................... 356/430 |
| 5,818,592 | 10/1998 | Womack et al. ................... 356/357 |

FOREIGN PATENT DOCUMENTS 3-273141  12/1991  Japan .

*Primary Examiner*—Frank G. Font
*Assistant Examiner*—Zandra V. Smith
*Attorney, Agent, or Firm*—Beall Law Offices

[57] ABSTRACT

A magnetic disk testing method is provided, which comprises a surface defect test step of detecting, as defect data, the size of surface defect of a magnetic disk, the continuity thereof, the number thereof and the position thereof by testing magnetic disks optically and a classification step of classifying the magnetic disks to first magnetic disks, second magnetic disk and third magnetic disks on the basis of the defect data obtained in the surface defect test step. The first magnetic disks have surface defects which do not provide any problem on electric characteristics and are to be qualified through a subsequent certification test, the second magnetic disks require a further certification test for determining whether or not the surface defects thereof provide a problem on electric characteristics and the third magnetic disks have electric characteristics which are to be clearly disqualified without necessity of a further certification test, wherein the first magnetic disks are decided as qualified and the second magnetic disks are objects for the certifying test.

17 Claims, 7 Drawing Sheets

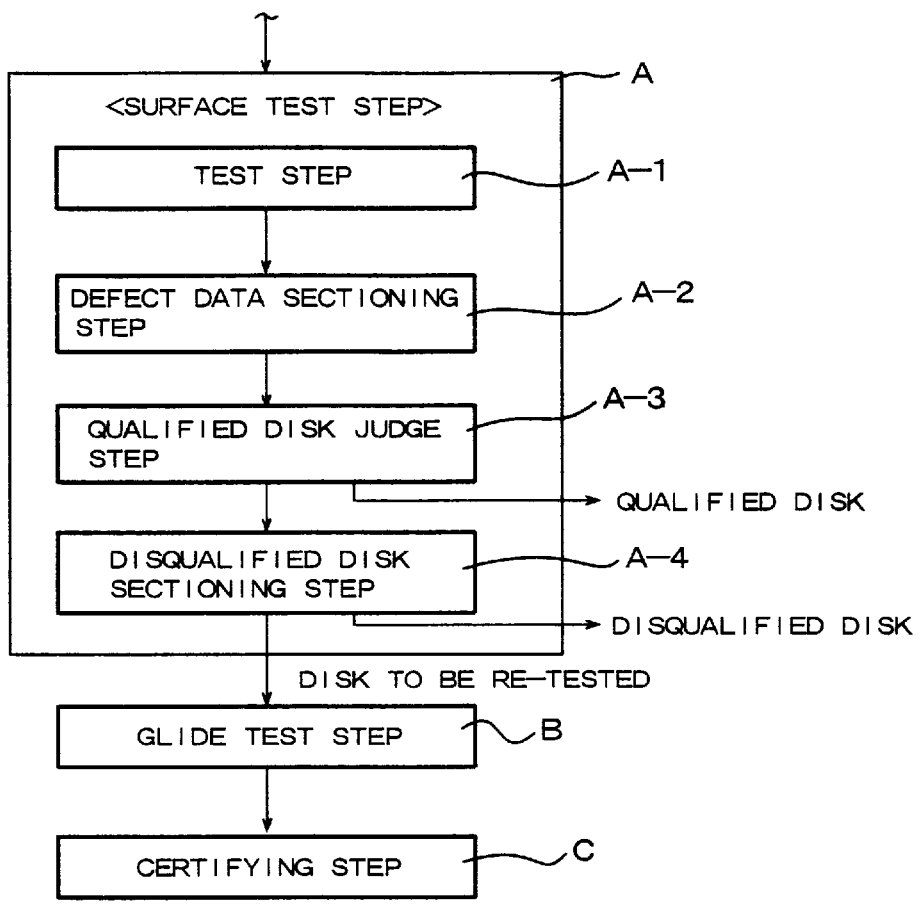
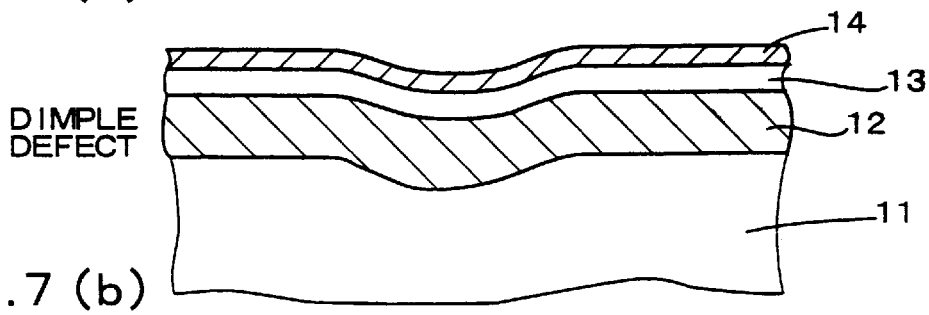
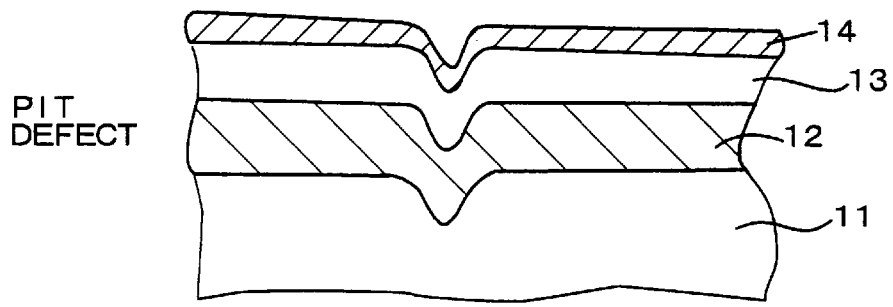

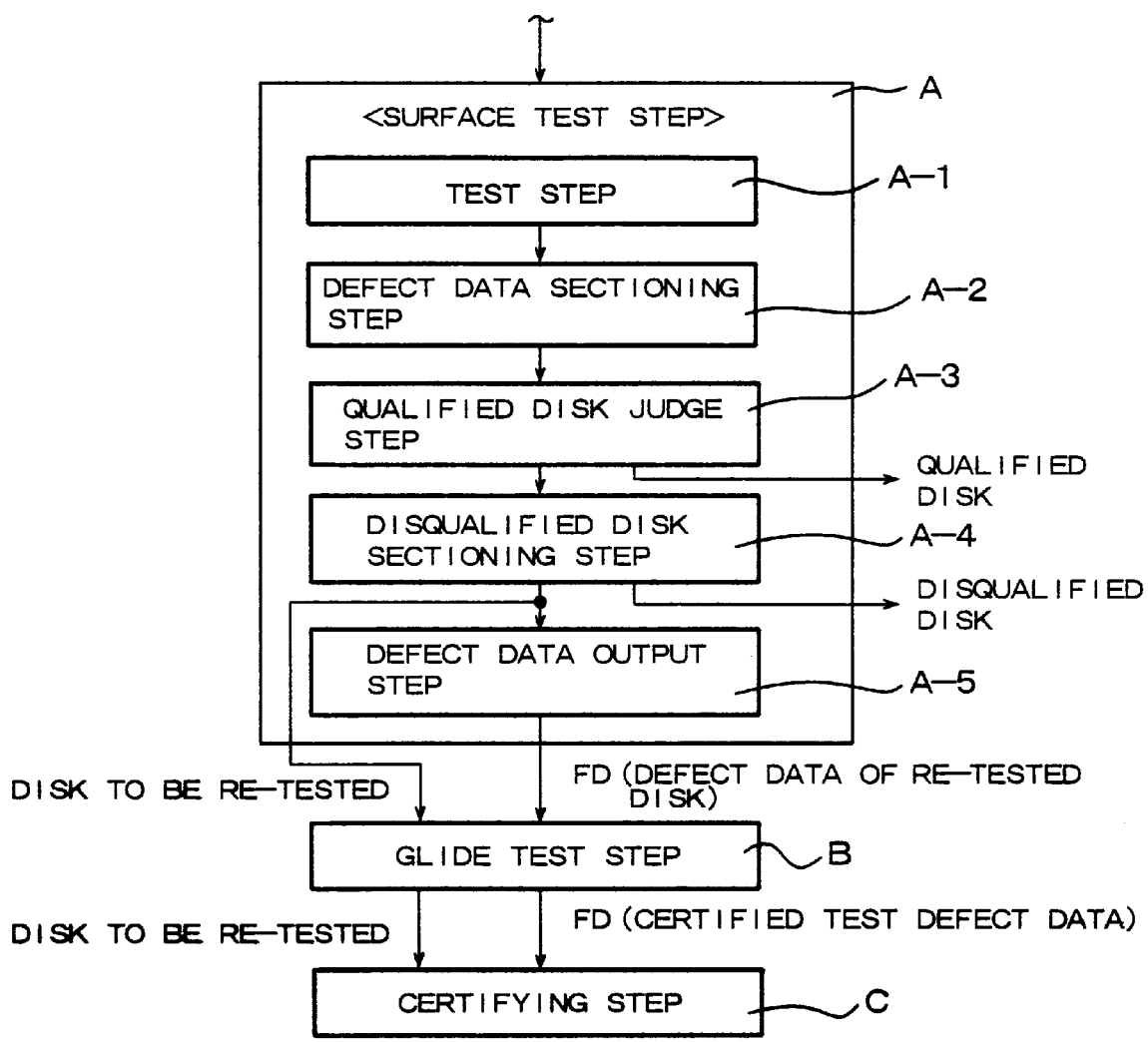

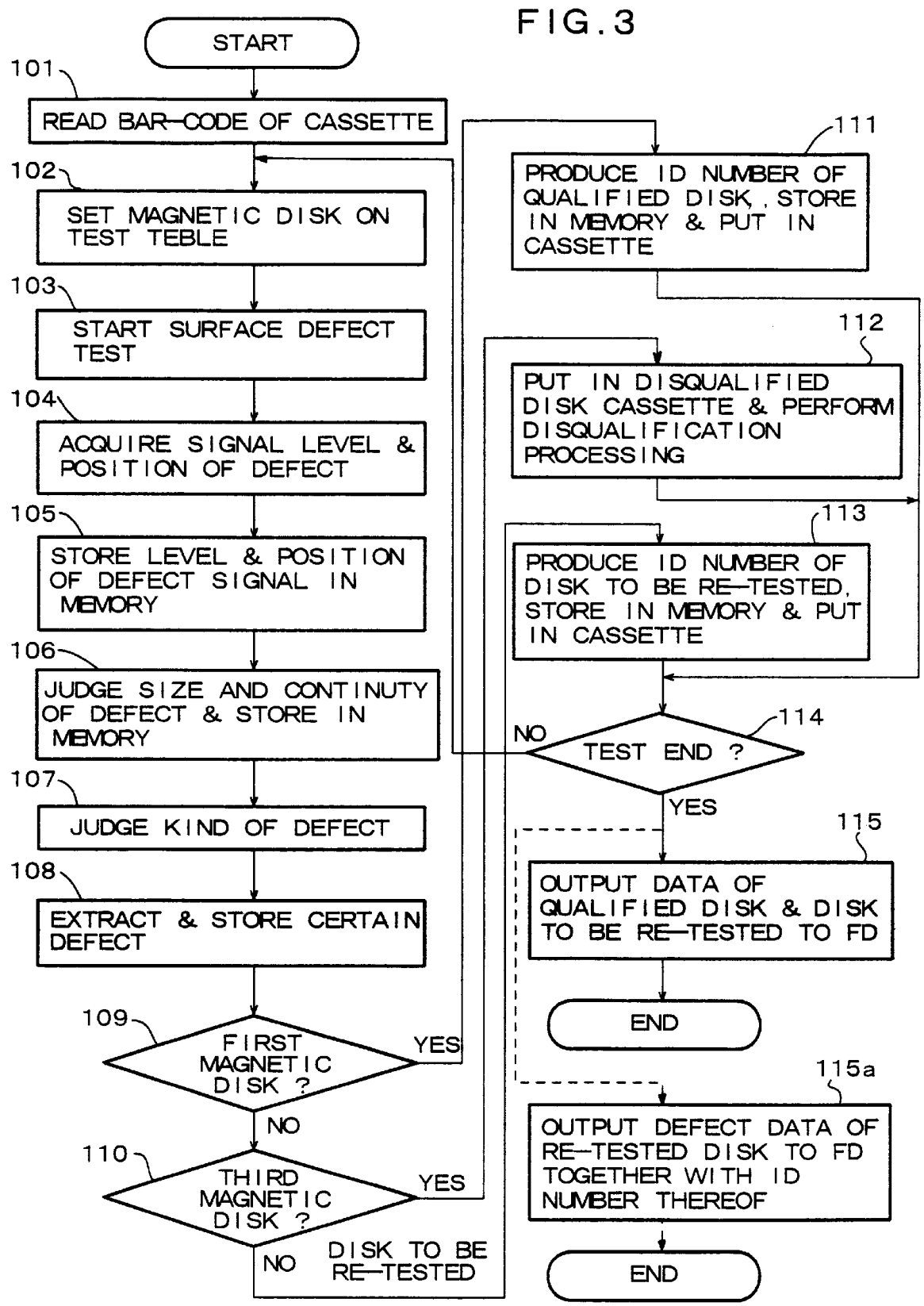

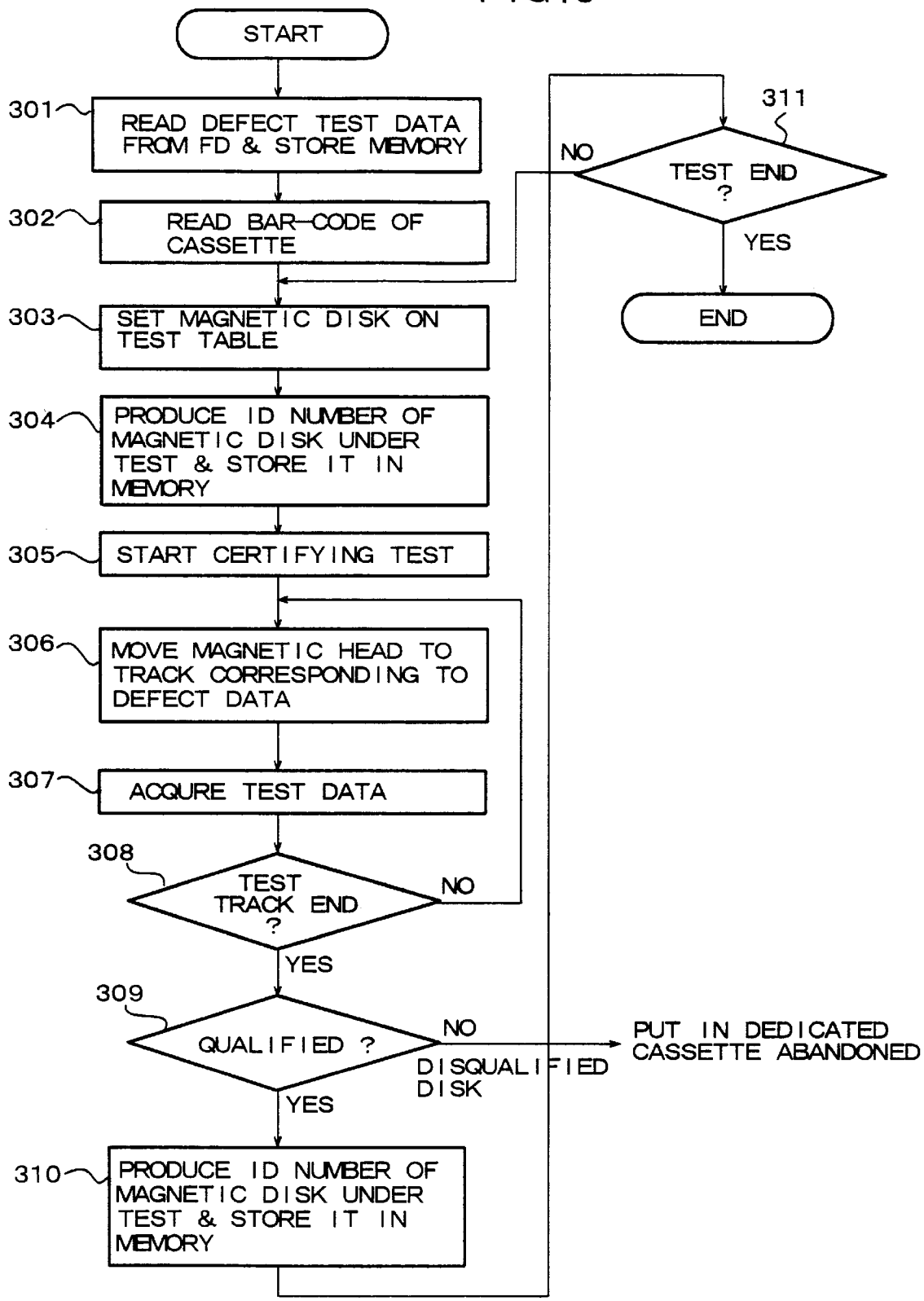

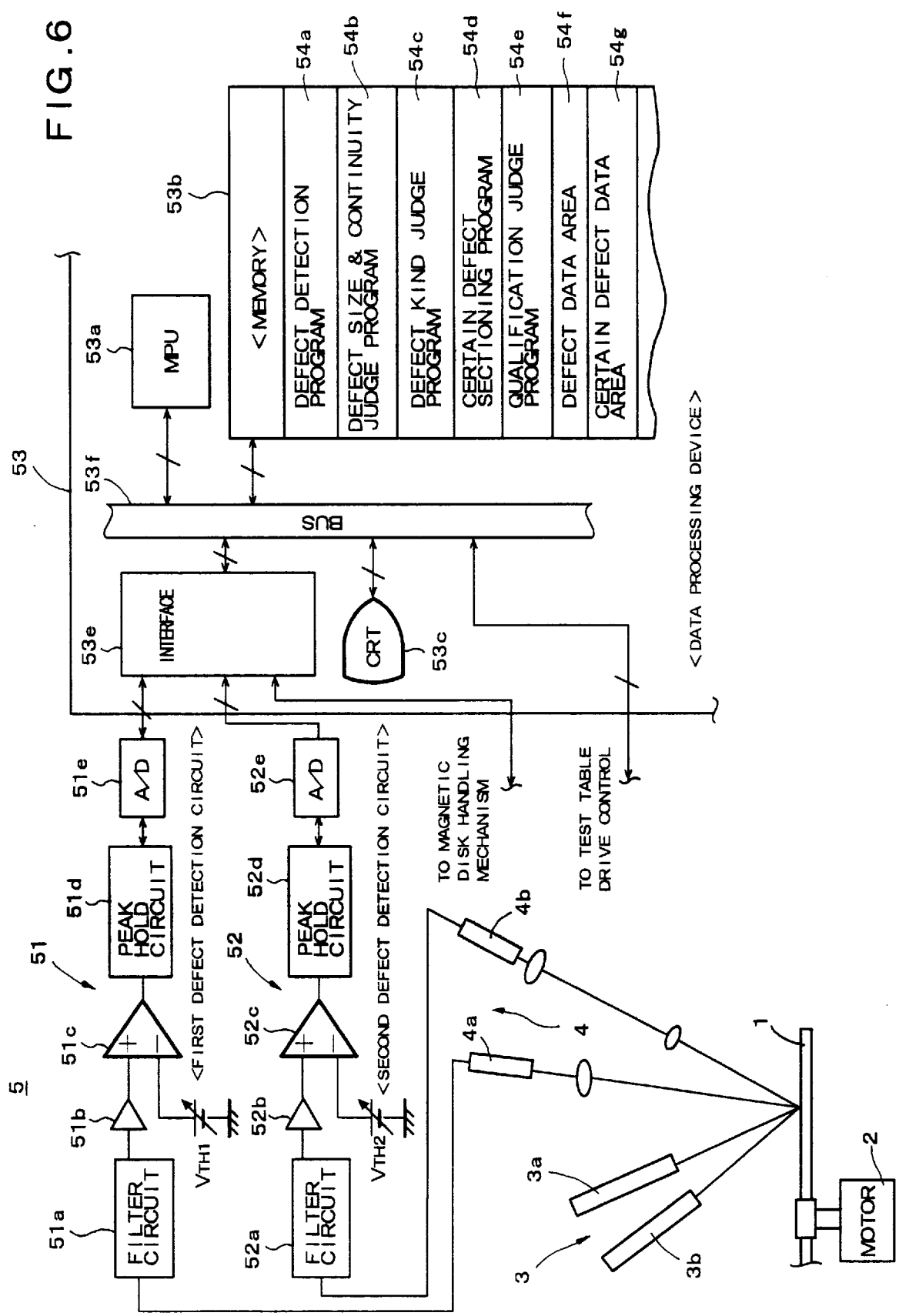

MAGNETIC DISK TESTING METHOD AND SURFACE DEFECT TESTING DEVICE

BACKGROUND OF THE INVENTION

1. Technical Field

The present invention relates to a magnetic disk testing method and a surface defect testing device and, particularly, to a magnetic disk testing method and a surface defect testing device with which the throughput of test of magnetic disks for high density recording can be improved.

2. Background Art

A hard disk device (HDD) which is one of external memory devices of a computer uses a hard magnetic disk as its recording medium. The magnetic disk is fabricated by forming a magnetic film on a surface of a circular disk of such as aluminum or glass by painting, and coating the magnetic film with a protective film. The surface of the circular disk having the magnetic film and the protective film thereon is preferably a flat plane having as small irregularity such as protrusions as possible and has a good recording performance. The smoothness of the surface of the magnetic disk is tested by a glide tester and the electric recording performance thereof is tested by a certifier.

The number of tracks of a magnetic disk for high recording density is large and the efficiency of test of the magnetic disk is lowered with increase of the recording density of the magnetic disk. In order to improve the yield and the test efficiency of magnetic disk in the glide tester, it is a recent tendency to provide an optical surface defect test step between a varnishing step and a glide test step. The glide test is performed after defective disks are preliminarily removed by optically testing surface defects of the magnetic disks in the surface defect test step.

FIG. 8 shows a conventional fabrication and test steps of a magnetic disk. First, there is a magnetic film forming step (1) in which a magnetic film and a protective film are formed on a disk of such as aluminum by painting, in the order, and, then, in order to make the irregularity of surface of the magnetic disk having the magnetic film and the protective film formed thereon as small as possible, protrusions on the surface are removed in appearance through a varnishing step (2). Then, the surface defect of the magnetic disk is evaluated in a surface defect test step (3). In the surface defect test step, disks having defects whose size exceeds a predetermined reference value are excluded and, then, tested in a glide test step (4). In the glide test step (4), the existence and the number of protrusions are detected by a glide test head. The glide test step (4) includes a varnishing step for lightly varnishing the magnetic disk. When, as a result of this test, it is found that there are residual protrusions the number of which exceeds a predetermined number, the result of test becomes no-good (NG) and the magnetic disk is returned to the varnishing step of the glide test step (4) to varnish the magnetic disk again. Magnetic disks which become good (G) in the glide test step (4) are processed in a certifying step (5).

Incidentally, an invention in which a glide test and a varnishing step are performed by one and the same device in the glide test step (4) was patented as U.S. Pat. No. 5,423,111.

The surface defect test step mentioned above is intended to improve the yield of magnetic disk in the glide tester and to do not test magnetic disks which may be certainly disqualified in the glide test step. However, the number of magnetic disks which become disqualified in the surface defect test step is practically very small with recent improvement of manufacturing preciseness of magnetic disk. Therefore, the test throughput (test efficiency) per magnetic disk for high density recording is not improved substantially even when such surface defect test step is introduced.

SUMMARY OF THE INVENTION

An object of the present invention is to provide a magnetic disk test method capable of improving the throughput of test of magnetic disks for high density recording to thereby solve such problem of the conventional technology.

Another object of the present invention is to provide a magnetic disk defect testing device capable of improving the throughput of test of magnetic disks for high density recording.

In order to achieve the above objects, a magnetic disk test method according to the present invention is featured by comprising a surface defect test step of optically testing a magnetic disk to detect the size of surface defect, the continuity thereof, the number of surface defects and the position of surface defect with higher accuracy than that of a test of an electrical characteristics of a magnetic disk in a certifying test step to thereby obtain a defect data and a classification step of classifying magnetic disk on the basis of the defect data obtained in the surface defect test step to first magnetic disks whose surface defects do not provide any problem on electric characteristics of the magnetic disks and which are to be passed through the certifying test step, second magnetic disks which require a further certifying test for determining whether or not surface defects thereof provide a problem on electric characteristics of the magnetic disks and third magnetic disks which have electric characteristics to be certainly rejected without necessity of a further certifying test, wherein the first magnetic disks are decided as being qualified and the second magnetic disks are decided as to be tested in the certifying test step. With using this method, it is possible to improve the efficiency of certifying test step.

Further, a magnetic disk testing device according to the present invention comprises test means for realizing the above mentioned surface defect test step and classification means for realizing the classification step.

By the way, the main difference between the optical test of surface defect of a magnetic disk and the certifying test of a magnetic disk is that the former detects the configuration of surface of magnetic disk optically while the latter electrically detects defects influencing the electric characteristics of magnetic disk by means of a magnetic head. Therefore, a result of the former optical test is not always coincident with a result of the latter electrical test. However, it is possible to select, in an optical surface test, magnetic disks which certainly become qualified in also the electrical test by making the preciseness of the optical surface test higher to provide a high selection reference of qualified magnetic disk. As the selection reference, the size of defect, the continuity of defect, the number of defects and the position of defect are used in this invention.

That is, in the above mentioned test method and surface defect test device, a magnetic disk is classified to one of three kinds of magnetic disk, that is, first, second and third magnetic disks according to surface defect of the magnetic disk. In order to classify the magnetic disks in this manner, the size of defect of the magnetic disk, the continuity of defect, the number of defects and the position of defect are obtained in the surface defect test step. Particularly, the size of defect is obtained under more severe condition than the conventional surface defect test condition shown in FIG. 8.

By classifying magnetic disks under test to the three classes in the surface defect test step, magnetic disks which become qualified are determined in this step without using the glide test and the certifying test. In view of the fact that the number of qualified magnetic disks is dominant with respect to the number of disqualified magnetic disks, as mentioned previously, it is possible to obtain qualified magnetic disks which have electric characteristics to be qualified and which may be about 30% or more of a total number of magnetic disks which have optical defects in view of the defect data obtained by performing the surface defect test with high precision. As a result, it is possible to reduce the number of magnetic disks to be tested in the glide test and the certification test by 70% or smaller of the total number of magnetic disks.

Thus, the magnetic disks to be tested become 70% of the total number of magnetic disks to be tested by the conventional method and it is possible to improve the efficiency of magnetic disk test as a whole.

According to another embodiment of the present invention, the surface defect test method comprises, in addition to the steps mentioned above, a defect data output step for providing at least defect position data of the second magnetic disks classified in the classification step and an identification information for identifying the second magnetic disks as a defect information to be utilized in the subsequent test step. Correspondingly thereto, the magnetic disk test device according to another embodiment of the present invention comprises defect data output means for realizing the above mentioned defect data output step.

By providing the defect data of the second magnetic disk for use in the subsequent test step, such as a glide test step and/or a cerytifying step, in this manner, it is possible to test concentrically a position of a magnetic disk in which a surface defect is detected while roughly testing or not testing the remaining positions of the magnetic disk in the subsequent test step. Thus, the throughput of test for one magnetic disk can be further improved.

A magnetic disk having some defect frequently becomes usable practically by a provision of alternative tracks or alternative sectors or by a one-bit error correction, etc. In view of this, among the three classes of magnetic disk, it becomes particularly important to classify and test the second magnetic disks. However, it is difficult practically to precisely classify the second magnetic disks separately from the third magnetic disks according to mere the size and position of defect and the number of defects. When the number of the third magnetic disks is large, the yield of magnetic disk is reduced and the number of magnetic disks which become wastes is increased. That is, the reduction of yield is a problem even if the test efficiency is improved. Therefore, in order to improve the preciseness of separation of the second magnetic disks from the third magnetic disks, the continuity of defect and the type of defect are employed in the present invention in addition to the size, position and number of defects.

Describing this in more detail, the surface conditions of magnetic disk such as shown by partial cross sections in FIGS. 7(a) and 7(b) are detected as surface defects in the optical defect test.

FIG. 7(a) shows a case where there is a shallow recess type defect usually called "dimple" in a disk substrate including a plated layer and a magnetic film is formed thereon. However, the number of magnetic disks which have magnetic films detected as having such shallow recess, nevertheless, can guarantee data read/write thereto is not small although an electric data output level is lowered more or less. On the other hand, FIG. 7(b) shows a case where there is a deep hole type defect usually called "pit" in a disk substrate on which a magnetic film is formed. In the case of such deep hole type defect, a magnetic film itself becomes thin locally or there is substantially no magnetic film formed locally on a surface of the magnetic disk. In such case, data read/write with respect to the magnetic disk is not guaranteed frequently.

For these reasons, the preciseness in the optical defect test step is made higher and the continuity of defect and the aforementioned type data are employed as defect data in addition to the size and number of defects.

That is, in order to more precisely separate the second and third magnetic disks from magnetic disks disqualified in the optical defect test, magnetic disks which have surface defects in the form of shallow recesses called dimples such as shown in FIG. 7(a) are excluded from qualification reference. In order to do so, the continuity of defect and the type of defect are referenced. It is general in the optical defect test that a dimple appears as a surface defect having a relatively short length and a some area. Such defect is excluded from the defect data for classifying the second and third magnetic disks and it is determined whether or not the defect becomes problems in the subsequent certifying test step. In the latter step, such type of defect becomes an uncertain defect to be described later.

On the other hand, the pit type defect has no continuity and appears as a short discrete defect. A disk having deep pits, data read/write for which are not guaranteed with respect to a magnetic disk and the number of which exceeds a reference number, is classified as the third magnetic disk. A magnetic disk which has a predetermined number of long defects which are usually disqualified in views of the continuity and the type is also extracted as a third magnetic disk. A magnetic disk having defect which causes the alternative track or alternative sector to be impossible is classified and extracted as a third magnetic disk. The classifying condition of these magnetic disks classified as the third magnetic disks is determined by repeating the certifying operation for actual magnetic disks having these types of defects.

In concrete, magnetic disks which are judged as the third magnetic disks are those having, as defects by which data read/write with respect thereto can not be guaranteed, pit type defects large enough to make 1 bit correction impossible, which make alternative track or alternative sector impossible in view of the number of the pits, the positions thereof and the continuity thereof, those having such pit type defects the number of which exceeds a value with which usual alternative track or alternative sector is impossible, those having continuous type defects longer than a reference value and/or those having a predetermined amount of continuous type defects having length exceeding a predetermined value. The remaining magnetic disks are decided as the second magnetic disks. The long continuous type defect may be a groove type scratch, etc.

On the other hand, when the preciseness of the optical surface test is made high, the number of the second and third magnetic disks which necessarily become disqualified with respect to the first, qualified magnetic disks become increased, causing the separation of the second magnetic disks from the third magnetic disks to be difficult. In the present invention, however, the second magnetic disks are further separated from the third magnetic disks in the certifying step in view of the pit type defect in addition to the defects which usually cause related magnetic disks to be disqualified, as mentioned above. By extracting the third, disqualified magnetic disks from the magnetic disks disqualified in the optical defect test in view of the number of pits, the size thereof and the continuity thereof, the remaining magnetic disks can be classified as the second magnetic disks precisely and, thus, it is possible to improve the total test efficiency by testing only the second magnetic disks in the certifying test.

Incidentally, in FIG. 7, a reference numeral 11 depicts a disk substrate, 12 a plated layer of such as nickel alloy, 13 a sputtered magnetic film and 14 a lubrication layer.

The above description of the recess type and hole type defects is also applicable to protrusion type defect. As to a gentle protrusion type defect called "mound", there are many magnetic disks having such protrusion type defect, which can guarantee data read/write with respect thereto, since a relatively thick magnetic film is formed around the mound. However, as to protrusion type defect called "bump", a magnetic film itself may be locally broken by the bump and substantially lost or locally thinned. Therefore, there are many cases where data read/write with respect to a magnetic disk having such type defect is not guaranteed. By considering the number of bumps, the size thereof and the continuity thereof with using the magnetic disks having the latter defect as a reference similarly to the case of the pit type defect, it becomes possible to precisely separate the third magnetic disks to be disqualified from the second magnetic disks which have defects to be tested in the certifying step. Incidentally, the mound type defect becomes the uncertain defect to be described later.

In the recent surface defect test, the type of defect, such as dimple, pit, mound, bump and scratch, etc., of a magnetic disk can be detected, respectively.

By taking the type of defect into consideration, it becomes possible to precisely classify the third magnetic disks from the second magnetic disks which have defects to be tested in the certifying step, except uncertain defects prior to the electrical characteristics test in view of a relation between the size, the continuity and the type of defect and, thus, it becomes possible to decide the second magnetic disks to be tested.

BRIEF DESCRIPTION OF THE DRAWINGS

FIG. 1 shows a flowchart of a general processing of magnetic disk, to which the magnetic disk test method of an embodiment of the present invention is applied;

FIG. 2 is a flowchart of a general processing of magnetic disk, to which another embodiment of the present invention is applied;

FIG. 3 is a flowchart of a surface defect test method of the present invention;

FIG. 5 is a flowchart of a certifying test of the magnetic disk defect test method of the present invention;

FIG. 6 is a block diagram of a magnetic disk defect test device of the present invention;

FIG. 7 shows partial cross sections of typical surface defects of a magnetic disk, in which FIG. 7(a) shows a dimple type defect and FIG. 7(b) shows a pit type defect.

DETAILED DESCRIPTION OF THE PREFERRED EMBODIMENTS

Figure 8:
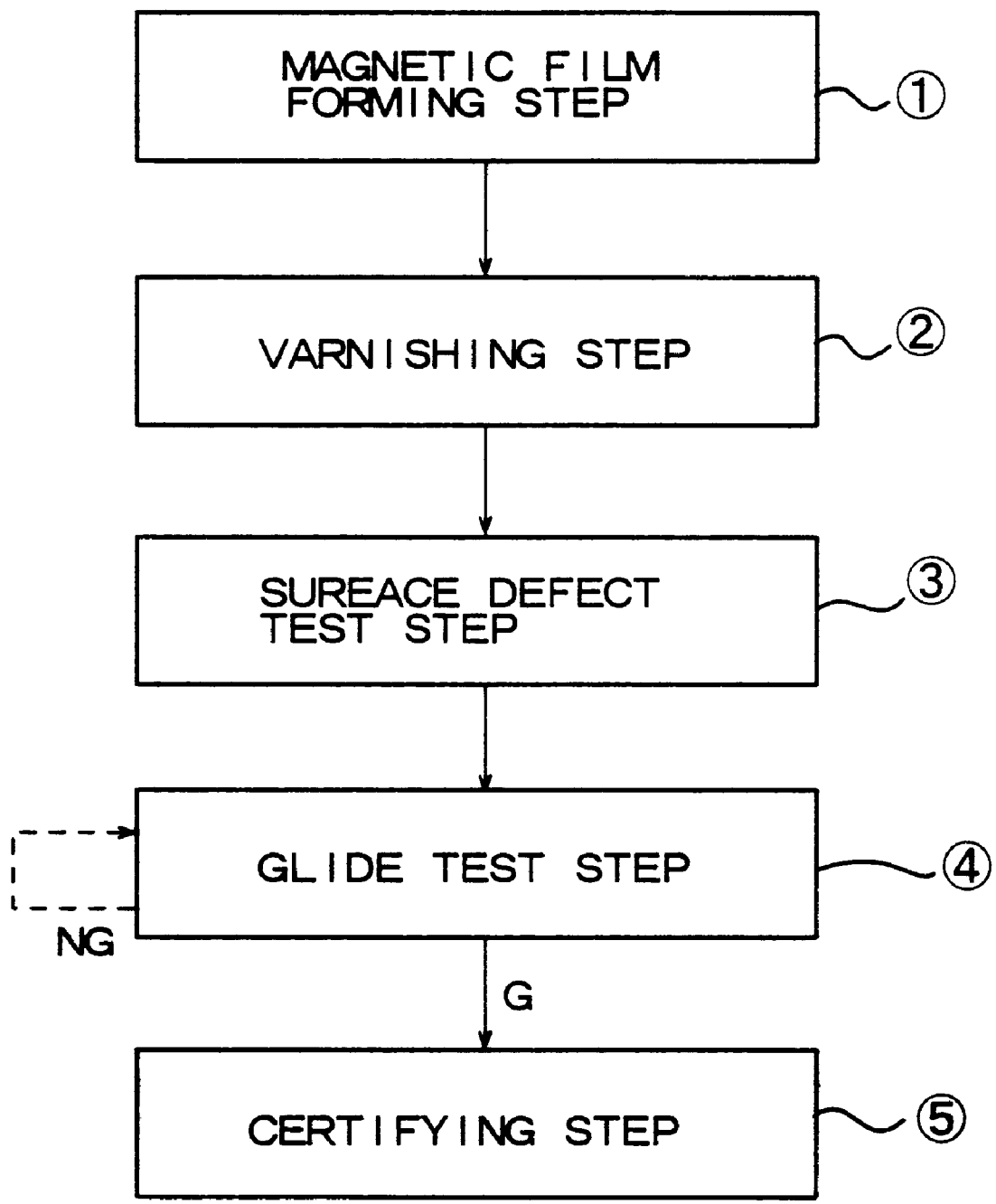
FIG. 8 shows a flowchart of a conventional magnetic disk manufacturing and test step.

In FIG. 1 which is a flowchart of a whole processing of magnetic disk, to which a magnetic disk test method according to the present invention is applied, capital letter A depicts a surface defect test procedure which corresponds to the surface defect test step (3) shown in FIG. 8. This procedure A is composed of a test step A-1, a defect data sectioning step A-2 and a qualified disk decision step A-3 and a disqualified magnetic disk sectioning step A-4, for classifying tested magnetic disks to the first, second and third magnetic disks.

The test step A-1 is to obtain the size of magnetic disk defect, the continuity thereof, the number thereof, the type thereof and the position of defect of magnetic disk, as the defect data. The defect data sectioning step A-2 is to separate, from the thus obtained defect data, data of uncertain defect which may guarantee the data read/write with respect to a magnetic disk related thereto electrically while it is uncertain whether or not it is a defect in view of the electrical characteristics test in the certifying test step and data of certain defect which is certainly decided as defect on the electrical characteristics.

Decision of the certain defect or the uncertain defect depends upon whether or not a data read/write with respect to a magnetic disk related thereto is guaranteed in view of the type of defect such as dimple, pit, mound, bump or scratch. etc., the position thereof and/or the continuity thereof. That is, defects with which a data read/write with respect to a related magnetic disk can not be guaranteed are the certain defects and other defects become uncertain defects. The certain defect includes pit or dimple having a size which does not allow 1-bit correction, a defect with which the data read/write with respect to a related magnetic disk can not be guaranteed in view of the position and length thereof and a defect which continues for a distance larger than a constant distance regardless of the position thereof, etc.

Selecting condition of such certain defects with which data read/write with respect to related magnetic disk is not guaranteed is decided by repeatedly writing data of practically existing defects on magnetic disks and electrically reading it in a certifier and by confirming whether or not the defects guarantee data read/write thereto.

The qualified disk decision step A-3 is to determine, on the basis of the defect data acquired initially, the first magnetic disks which have no problem with respect to the electric characteristics thereof and become qualified in the certifying test and to qualify the first magnetic disks without electric characteristics test. The first magnetic disk has defects the number of which is smaller than a predetermined number, a predetermined number of which are not concentrated in a specific track of the magnetic disk or sector thereof and with which the data read/write with respect to the magnetic disk is guaranteed. Further, the selecting condition of the defects with which the data read/write with respect to a related magnetic disk is guaranteed is determined by repeatedly writing and electrically reading data of practically existing defects in the certifier and confirming whether or not data read/write is guaranteed.

The disqualified magnetic disk sectioning step A-4 is to extract, from the magnetic disks which become disqualified in the qualified disk decision step A-3, the third magnetic disks which will be disqualified certainly in the defect data sectioning step A-2, to separate the remaining magnetic disks as the second magnetic disks to be tested in the certifying test from the disqualified magnetic disks and to make the second magnetic disks as disks to be tested again.

The magnetic disk which will be certainly disqualified is decided in view of the certain defects, the number thereof and the position thereof. Particularly, the position of defect depends upon the number of certain defects in one and the same track or sector of the magnetic disk and the continuity of these defects. Since, when the number of the certain defects exceeds a predetermined constant value, an alternative track or alternative sector becomes not available, the magnetic disk is certainly decided as to be disqualified when the number of the certain defects exceeds the predetermined value. Further, the magnetic disk is certainly decided as to be disqualified dependently upon the number of continuous defects which are longer than a reference value or whether the position thereof makes the alternative track or alternative sector impossible to provide. Further, the magnetic disk is certainly decided as to be disqualified according to the degree of concentration of continuous defects longer than a predetermined length in a specific track or sector.

Capital letter B in FIG. 1 shows a glide test step which corresponds to the glide test step (4) in FIG. 8, which is to perform the glide test for all tracks (whole surface) of the second magnetic disks which is to be tested again.

Capital letter C shows a certifying test step which corresponds to the certification test step (5) in FIG. 8. This step is to perform a certifying test for all tracks (whole surface) of the second magnetic disks which are qualified in the glide test step B.

FIG. 2 shows a flowchart of another embodiment of the surface defect test which differs from that shown in FIG. 1 in that a defect data output step A-5 is added to the disqualified magneic disk sectioning step A-4 in FIG. 1 as the last step thereof. The added step A-5 is to output an identification (ID) number and defect data (data of defect prior to extraction of the data of certain defect data) of the second magnetic disk to be tested again to a recording medium such as floppy disk (FD).

The defect data output step A-5 outputs defect data to be used in the subsequent test step, which includes uncertain defect data and certain defect data prior to separation in the defect data sectioning step A-2, to the floppy disk together with the ID number of the second magnetic disk. In this case, the data of the uncertain defect and the data of the certain defect are stored in the floppy disk separately:

The defect data output to the recording medium includes at least the position data of defect on the magnetic disk. The ID number of the magnetic disk is managed by the manufacturing lot number of the magnetic disk, the number of disk cassette in which the magnetic disk is housed and a numeral indicative of loading position of the disk cassette (for example, a sequence number of the disk cassette). The lot number and the disk cassette number are specified by a bar-code label attached to a side surface of the disc cassette, which can be read out optically by the magneic disk defect test device. The loading position of the magnetic disk cassette corresponds to the sequence number since the sequence of loading thereof is managed by a handling arm of the magnetic disk defect test device.

A glide test step B shown in FIG. 2 differs from the glide test step in FIG. 1 in that, although disks to be tested again (second magnetic disks) obtained after the disqualified magnetic disk sectioning step A-4 are processed as in the case of the embodiment shown in FIG. 1, the glide test processing in the step B in FIG. 2 is performed not for a whole surface of a magnetic disk unlike the case shown in FIG. 1 but for a position at which a defect is detected on the basis of the defect data output from the defect data output step A-5, an area before and behind the defect position including the latter or a sector or track in which a defect exists. With this processing, an efficient test can be done. Further, the defect data obtained by the slide test is output to the floppy disk for use in a subsequent test step.

In concrete, in the glide test step B in FIG. 2, the defect test data of the second magnetic disk obtained in the defect data output step A-5 is read from the floppy disk and the ID number of the magnetic disk to be tested is read out from the bar-code of the disk cassette and the pick-up position of the cassette and the detailed glide test is performed for the defect position of the defect data, the area before and behind the defect position including the latter or the track or sector in which the defect position. Magnetic disks disqualified in this test are tested again after varnishing them in the glide test step. The magnetic disk qualified in this test step is loaded in a disk cassette and, then, a bar-code label on the side faces of the disk cassette is read, a new ID number is produced from the loading position of the cassette, the initial ID number thereof is replaced by the newly produced ID number and the latter is written in the floppy disk. In this case, the lot number of the disk cassette is not changed unless there is any special condition.

In the certifying step C succeeding to the glide test step B, the defect data detected in the glide test step B is read from the floppy disk and the certifying test is performed for the defect position of the defect data, the area before and behind the defect position including the latter or the track or sector in which the defect position, on the basis of the defect data thus read out.

In concrete, in the certifying step C, the defect data detected in the glide test step B is read from the floppy disk, the ID number of the disk to be tested is read out from the bar-code on the disk cassette and the cassette pick-up position and the detailed certifying test is performed for the defect position of the defect data, the area before and behind the defect position including the latter or the track or sector in which the defect position, according to the position data. Magnetic disks disqualified in the certifying step are abandoned.

FIG. 3 is a flowchart of the surface defect test method according to the embodiments shown in FIGS. 1 and 2.

Describing the flow of the embodiment shown in FIG. 1, a bar-code is read out from a disc cassette of the magnetic disk passed through the varnishing step (2), a bar-code is read out from a bar-code label of a disk cassette and stored in a memory (step 101), a magnetic disk to be tested is set on a spindle of a test table (step 102), and the surface defect test is started (step 103). Then, a signal level of the defect detected and its position on the disk are acquired (step 104) and the level data and the position data of the defect signal are stored in the memory (step 105). Then, the size and continuity of the defect are determined on the basis of the level data and position data of the defect signal, and data of them are produced and data thereof is stored in the memory (step 106). Further, the above mentioned continuity and the type of defect are determined by, for example, one of the two light receiving detector systems to be described with reference to the embodiment shown in FIG. 6 (step 107). Then, certain defect data is determined by excluding uncertain defects on the basis of the size of defect, the continuity and the kind of the defect and stored in the memory (step 108). The remaining certain defects which may be dimple or mound as mentioned previously may be stored in another memory area as uncertain defect data.

From the magnitude, the continuity, the number and the position of the defect signal in the defect data before the classification of the certain defect data (not including the kind of defect), it is determined whether or not the magnetic disk is the first magnetic disk (step 109). When it is the first magnetic disk, it is qualified in this state and the glide test step B and the certification step C are not performed basically. That is, the magnetic disk is basically inspected by sampling in the glide test step B and the certifying test step C or in the certifying test step to confirm the reliability of decision of magnetic disk qualified in the optical test on demand and, according to the result thereof, the judge condition is changed such that the judgement becomes more reliable.

For the magnetic disks which were disqualified in the step 109, it is determined, with reference to the determined defect data produced in the step 108, whether or not they are the third magnetic disks which are to be certainly disqualified and the remaining magnetic disks are determined as the second magnetic disks to be tested again (step 110).

Then, for the first magnetic disks which were qualified in the step 109, they are put in disk cassettes, and ID number (lot number+cassette number+storage position) is produced by the acquired storage position data and stored in the memory as the qualification data (step 111). For the third magnetic disks which were disqualified in the step 110, those disqualified are stored in disk cassettes for disqualified disks and processed as disqualified (step 112).

For the second magnetic disks which were qualified by the judgement in the step 110, ID numbers (lot numbers+ cassette numbers+storage positions) of the magnetic disks and their defect data (defect data prior to separation of the certain defect data) are stored in the memory as disks to be tested again (step 113). And, by determining whether or not there are magnetic disks in a predetermined cassette, it is determined whether or not the surface defect test is completed (step 114). When it is not completed as yet, the processing is returned to the step 102. When completed, the qualified data in the step 111, the defect data in the step 112 are tabled together with the ID numbers and output to a floppy disk (FD) (step 115).

When the qualified first and second magnetic disks are stored not in the their original disk cassettes but in new disk cassettes, the bar-codes of the new disk cassettes are read to produce a new identification information.

Although the determination of whether or not the magnetic disks are qualified is performed on the basis of the size of defect, the continuity thereof and the number of defects existing in, for example, 1 track or sector as mentioned above, the judgement of uncertain defect in the step 108 is based on the type of defect and the continuity thereof. Incidentally, the size of defect is determined by the signal level.

The flowchart shown in FIG. 3 and described hereinbefore is for the embodiment shown in FIG. 1 as mentioned previously. In the case of the embodiment shown in FIG. 2, the processing in the step 115 is replaced by a processing in a step 115a as shown by a dotted line in FIG. 3. That is, when it is decided in the step 114 that the test is completed, the defect data of the second magnetic disks acquired in the step 112 is tabled together with the ID number thereof and the table is output to the floppy disk in the step 115a. In the glide test step B, the tabled defect data is read out from the floppy disk and the glide test is performed concentrically in the position of defect obtained from the defect data. Further, in the glide test step B, the defect data is tabled together with the ID number of the magnetic disk and output to the floppy disk similarly. The defect data is read out from the floppy disk in the certifying step C and the certifying test is performed concentrically in the position of defect obtained from the defect data.

Figure 4:
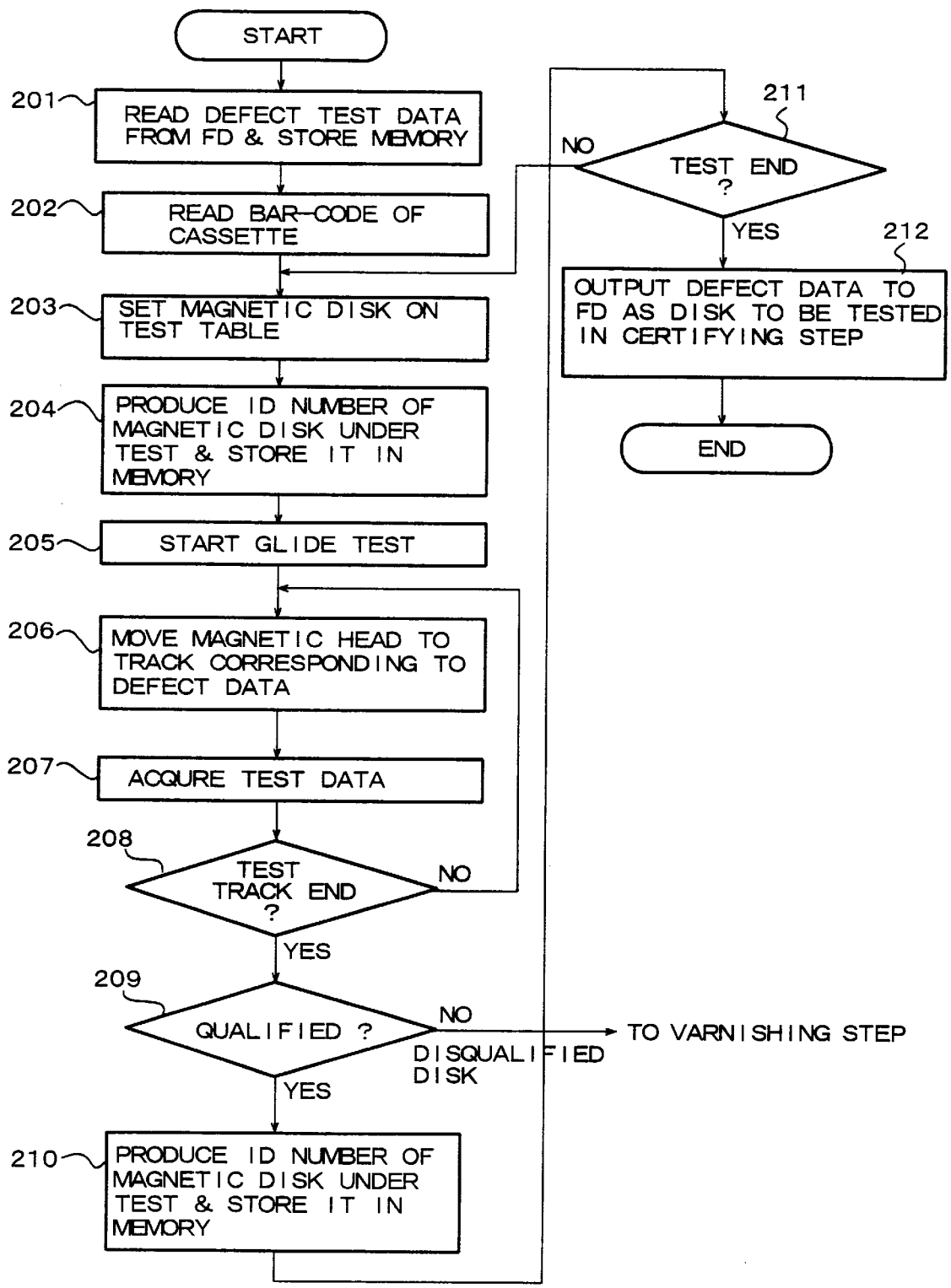
FIG. 4 is a flowchart of a glide test in the magnetic disk defect test method of the present invention.

The glide test step B in the case of the embodiment shown in FIG. 2 will be described in detail with reference to the flowchart shown in FIG. 4.

First, the defect test data stored in the floppy disk in the step 115a is read in the memory (step 201), the bar-code of the bar-code label of the disk cassette is read and stored in a memory (step 202), the magnetic disk to be tested is set on the test table (step 203) and an ID number (lot number+ cassette number+pick-up position) is produced by obtaining the pick-up position of the cassette and stored in the memory (step 204). Then, the glide test is started (step 205).

Next, the glide test head seeks a track of the magnetic disk corresponding to the position of defect data and performs the defect test of the defect position of the defect data, the area before and behind the defect position including the latter or the track or sector in which the defect position exists (step 206) and the test data is acquired (step 207). Then, it is decided whether or not the test track is ended (step 208). When there is a further defect data, the processing is returned to the step 206 and the glide test head seeks a next track having defect and acquires a test data. This is repeated until the test of all tracks having defects is completed. When the glide test data of the all tracks having defects are acquired, it is decided on the basis of the result of test whether or not the magnetic disk is qualified (step 209). Qualified magnetic disks are housed in respective disk cassettes and identification numbers (lot number+cassette number+storing position) thereof are produced according to the housing position data acquired (step 210) and, then, it is decided whether or not the test is completed (step 211). When there is a magnetic disk to be tested next in the cassette, the processing is returned to the step 203 and the tests are performed similarly.

When all of the tests for the magnetic disk stored in the cassette is completed, the test completion is decided in the step 211, the ID number of the tested magnetic disk, which was stored in the memory, is rewritten to the ID number produced in the step 210, the ID number in the floppy disk storing the defect data is updated (step 212), and, when the magnetic disk is qualified, the magnetic disk is sent to the subsequent certifying step C together with the disk cassette.

On the other hand, when the magnetic disk is disqualified in the steps 206 and 209, the disqualified magnetic disk is stored in another disk cassette and handled in a disqualifying process. In the disqualifying process, the disqualified magnetic disk is varnished in the glide test step and tested again through the steps 203 through 209. When the magnetic disk is disqualified in the steps a predetermined number of times, it is treated as wastes.

In returning the magnetic disk which is disqualified in the step 209 to the varnishing step in the glide test step, another ID number related to the initial ID number thereof is attached thereto.

Further, as mentioned above, when the qualified magnetic disk is not stored in its original disk cassette, the reading of the bar-code of the disk cassette in the step 202 is performed for a new disk cassette which stores the qualified magnetic disk.

Now, the certifying step C in the embodiment shown in FIG. 2 will be described in detail with reference to FIG. 5.

First, the defect test data read from the floppy disk whose identification information is updated in the step 212 is stored in the memory (step 301), the bar-code read from the bar-code label of the disk cassette is stored in the memory (step 302), the magnetic disk to be tested is set on the test table (step 303) and the ID number (lot number+cassette number+pick-up position) is produced from the pick-up position data of cassette and stored in the memory (step 304). Then, the certifying test is started (step 305).

Thereafter, the magnetic head seeks a track of the magnetic disk corresponding to the position of the defect data read from the floppy disk to test on defect for the defect position of the defect data, the area before and behind the defect position including the latter or the track or sector in which the defect position exists (step 306) and the test data is acquired (step 307). Then, it is decided whether or not the test track is ended (step 308). When there is a further defect data, the processing is returned to the step 306 and the glide test head seeks a next track having defect and acquires a test data. This is repeated until the test of all tracks having defects is completed. When the certifying test data for the tracks having defects are completed, it is decided on the basis of the test data obtained whether or not the magnetic disk is qualified (step 309). Qualified magnetic disks are stored in respective disk cassettes and ID numbers (lot number+cassette number+storing position) are produced according to the storing position data acquired (step 310) and, then, it is decided whether or not the test is completed (step 311). When there is a magnetic disk to be tested next in the cassette, the processing is returned to the step 303 and the tests are performed similarly. When the test for the magnetic disks stored in the cassettes is completed, the decision of test completion is made in the step 311, completing the certifying test.

Qualified magnetic disks are sent to an appearance test step together with their disk cassettes.

On the other hand, magnetic disks which are disqualified in the step 310 are stored in other disk cassettes for disqualified magnetic disks and processed as, for example, wastes.

FIG. 6 shows a construction of a magnetic disk test device of this kind. The detection processing performed by the magnetic disk test device will be described mainly in detail without detail of the scanning operation thereof. Such surface defect test device for detecting the kind of defect is described in, for example, U.S. Pat. No. 4,794,265 and Japanese Patent Application Laid-open No. Hei 3-273141 "Defect Detection Method of Magnetic Disk Magnetic Film and Detection Optical System", etc.

The surface defect test device 10 has two detection optical systems.

In FIG. 6, a magnetic disk 1 to be tested is rotated by a spindle motor 2 and helically scanned by a laser light. A projecting optical system 3 includes a first laser projecting light source 3a and a second laser projecting light source 3b. Laser projection angles of the first and second laser projecting light sources 3a and 3b are about 70°, respectively, and are arranged perpendicularly to each other in a horizontal plane, although shown differently for convenience of illustration. A light receiving system 4 corresponding to the light projecting system 3 and is composed of a first light receiving system 4a for receiving a regular reflection light which is projected by the first laser projecting light source 3a and reflected by the magnetic disk 1 and a second light receiving system 4b for receiving a regular reflection light which is projected by the second laser projecting light source 3b and reflected by the magnetic disk 1. Light receiving angles of the light receiving systems 4a and 4b are the same as those on the light projecting side and about 70°, respectively.

The difference between the first light projecting system 3a and the second light projecting system 3b resides in the thickness of laser beam. Laser beam emitted by the first light projecting system is a thin laser beam collimated as much as possible. In this point, laser beam emitted by the second light projecting system is a wide laser beam. With such difference, the first light receiving system 4a is used to detect pits and the second light receiving system 4b is used to detect dimples and mounds.

A defect detection circuit 5 includes a first defect detection circuit 51 and a second defect detection circuit 52 correspondingly to the first and second light receiving systems 4a and 4b, respectively.

The first defect detection circuit 51 is composed of a filter circuit 51a for receiving a detection signal of the first light receiving system 4a, an amplifier 51b for amplifying an output signal of this filter, a differential amplifier 51c for comparing an output signal of the amplifier 51b with a predetermined threshold value $V_{TH1}$ and amplifying a portion of the output signal which exceeds the threshold value, a peak hold circuit 51d and an A/D converter circuit 51e.

The second detection circuit 52 is composed of a filter circuit 52a for receiving a detection signal of the second light receiving system 4b, an amplifier 52b for amplifying an output signal of the filter circuit 52a, a differential amplifier 52c for comparing an output signal of the amplifier 52b with a predetermined threshold value $V_{TH2}$ and amplifying a portion of the output signal which exceeds the threshold value, a peak hold circuit 52d and an A/D converter circuit 52e.

The threshold values $V_{TH1}$ and $V_{TH2}$ are regulatable and are set to appropriate values correspondingly to states of the detection signals of the respective light receiving systems.

As a result, defects of the two systems which are detected correspondingly to the helical scan of the magnetic disk 1 are held in the respective peak hold circuits 51d and 52d. The values held in the respective peak hold circuits are converted into digital values by the A/D converter circuits 51e and 52e correspondingly to a control signal of a data processing unit 53 and taken in the data processing unit 53. The values held by the peak hold circuits 51d and 52d are reset by the signals from the respective A/D converter circuits 51e and 52e and peak values of next detection signals are held by them, respectively.

The data processing unit 53 is constructed with a micro processor unit (MPU) 53a, a memory 53b, a display 53c, a printer 53d and an interface 53e, etc., which are mutually connected through a bus 53f. In the memory 53b, a defect detection program 54a, a defect size and continuity judge program 54b, a defect type judge program 54c, decided defect sectioning program 54d and a qualification judge program 54e, etc., are stored and, further, a defect data area 54f and a decided defect data area 54g are provided therein.

The MPU 53a drives the spindle motor 2 through the interface 53e by executing the defect detection program 54a and starts the helical scan by controlling it to move in an X direction (or a Y direction). An amount of this control is stored in a predetermined area of the memory 53b as a scan position information. Then, the data of the A/D converter circuits 51e and 52e are taken in through the interface 53e with a predetermined timing and the detection levels are stored in the memory 53b correspondingly to the detectors of the first and second light receiving systems together with the scan position data, respectively.

The defect size and continuity judge program 54b is executed to read the defect data of the first and second light receiving systems which are acquired and stored in the memory 53b, to rank the sizes corresponding to the read defect data, to rise a flag in a range in which defect data of the respective first and second light receiving systems are continuous, to add the size information (data indicative of the size) thereto and to store them in the defect data area 54f together with the defect detection position data.

When, among the data stored in the defect data area 54f, there is defect data in the A/D converter circuit 51e whose level is within a predetermined value range and which has a continuity and there is no defect data in the A/D converter circuit 52e (or it is defect data whose level does not exceed a predetermined value), the defect type judge program 54c rises a flag indicating the defect data as a dimple or mound. This is the defect data which is defected in only the first light receiving system 4a for detecting dimple or mound or bump and has the continuity and low detection level. Therefore, the condition that there is no defect detected in the second light receiving system 4b for detecting pit is necessary.

The level of the defect data in the A/D converter circuit 51e within the predetermined value range is used to exclude bumps. The level of the detection signal becomes high when there is a bump. Further, the bump has almost no continuity.

The certain defect sectioning program 54d is executed to extract other defect than the defect which is determined as dimple or mound by the defect type judge program 54c as certain defect from the data in the defect data area 54f together with the size and continuity thereof and to store it in the certain defect data area 54g together with its position data. In such case, it may be possible to exclude the certain defect data from the data stored in the defect data area 54f and to make data in that area as uncertain defect data.

The qualification judge program 54e determines the first magnetic disks on the basis of the determination references of the size, the continuity, the number of defects and the position thereof from the data in the defect data area 54f and determines the third magnetic disks on the basis of the determination references of the size, the continuity, the number of defects and the position thereof from the data in the decided defect data area 54g.

As mentioned previously, a magnetic disk which certainly becomes qualified in the electrical test can be selected by the optical test by making the qualification reference of magnetic disk high by improving the preciseness of the optical surface test. Practically, however, the optical surface test for all defects is not always guaranteed in the certifying test due to the difference in characteristics between the optical surface test and the electrical test and there may be some difference between them because the optical test condition and the optical test environment which are varied to some extent influence on it. Further, there may be defects whose electrical and optical characteristics tests do not coincide dependently upon the material and thickness of the magnetic film and the material and polishing of the disk substrate.

Therefore, it is necessary as described previously to confirm the reliability of decision of magnetic disk to be qualified in the optical test by the certifying test of sampled first magnetic disks qualified in the optical surface test or change the test condition correspondingly to the state of test such that the decision becomes more reliable.

However, the quality of magnetic disks tested before the more reliable condition is set becomes a problem. However, it is possible to deal with such problem of the first magnetic disks by preventing degradation of the quality of manufactured magnetic disks by a sampling certifying test, a certifying test at rough pitch, a certifying test for a defect position and in the vicinity thereof or a combination of these tests.

The sampling test does not cause any degradation of the total test efficiency even if the sampling amount is increased to some extent, provided that all of the first magnetic disks qualified by the optical are not sampled.

The test for only the vicinity of a defect which is performed for the second magnetic disks in the described embodiment is performed for the first magnetic disk qualified in the optical surface test. That is, the defect position and the area in the vicinity thereof are tested on the basis of the defect data of the first magnetic disks. Further, the certifying test with rough track pitch is more efficient than that of the conventional whole surface test. The above mentioned matters are important in view of guarantee of magnetic disk quality and do not substantially degrade the test efficiency because the conventional certifying test is the whole surface test.

Although, in these embodiments, the defect type data is used as the defect data to classify defects to uncertain defects and certain defects, this classification may be to extract only certain defects from data of merely the size, the number and the position of defect by taking the continuity of defect into consideration, since it is enough to obtain the certain defects.

Further, as also described, it may be possible to qualify the uncertain defect as well as the certain defect by excluding certain defect data from the data in the defect data area 54f of the memory, providing only the position data of the remaining uncertain defect data of the defect data area and performing the glide test step B and the certifying step C for the position of the uncertain defect.

In the embodiments of the present invention, both the continuity of defect and the type of defect are considered in order to precisely classify the second and third magnetic disks. However, when only the continuity of defect is considered, only the number of the second magnetic disks may be increased. Therefore, it is still possible to improve the test efficiency since the first magnetic disks are not tested, and the consideration of the type of defect is not always indispensable requirement in the present invention.

Although the management of defect data is performed by using the floppy disk in the described embodiments, it is possible to use other memory medium than the floppy disk and it may be possible to transmit the defect data to the subsequent steps by utilizing an on-line network.

What is claimed is:

1. A magnetic disk testing method comprising the steps of:
   optically testing surface defects of magnetic disks by detecting the size of the surface defects, the continuity thereof, the number thereof and the position thereof to obtain a defect data; and
   classifying the magnetic disks having the surface defects thus tested in the optical test step to first magnetic disks, second magnetic disks and third magnetic disks on the basis of the defect data obtained in the surface defect test step, the first magnetic disks to be qualified in a subsequent test step, the second magnetic disks including magnetic disks to be decided as qualified in the subsequent test step, the third magnetic disks to be certainly disqualified in the subsequent test step.

2. A magnetic disk testing method as claimed in claim 1, wherein the defect data further includes the type of defect, and further comprising the step of glide-testing the second magnetic disks between the classifying step and a subsequent certifying step, only magnetic disks of the second magnetic disks, which are qualified in the glide test step, being tested in the subsequent test step.

3. A magnetic disk testing method as claimed in claim 2, further comprising the step of obtaining a defect information including the data of at least the position of defect and an identification information for identifying the second magnetic disks from the other magnetic disks, the second magnetic disks being tested in the glide test step or certifying step according to the defect information.

4. A magnetic disk testing method as claimed in claim 1, wherein the subsequent test step includes a glide test step and wherein a glide test is performed in a position of the surface defect of the second magnetic disk, an area in the vicinity of the position, a sector of the second magnetic disk including the position of defect or a track of the second magnetic disk including the position of defect according to the defect position data obtained correspondingly to the identification information of the second magnetic disks tested in the glide test step by reading the defect information obtained in the defect data obtaining step and a defect information of magnetic disks of the second magnetic disks which are qualified in the glide test step is newly produced according to a result of the glide test step.

5. A magnetic disk testing method as claimed in claim 4, wherein the subsequent test step further includes a step of certifying the second magnetic disks by reading the defect information obtained in the glide test step and testing the defect position of the second magnetic disk, an area around the defect position thereof, a sector including the defect position thereof or a track including the defect position thereof on the basis of the defect position data obtained from the new identification information.

6. A magnetic disk testing method as claimed in claim 2, wherein the type of defect includes defect with which a data read/write with respect to the magnetic disk is not guaranteed, wherein the classifying step is to extract first magnetic disks from the magnetic disks to be tested and to extract third magnetic disks from the remaining magnetic disks by referencing the defect with which the data read/write with respect thereto is not guaranteed.

7. A magnetic disk testing method as claimed in claim 6, wherein the defect with which the data reads/write with respect to the magnetic disks related thereto is not guaranteed is a pit type defect.

8. A magnetic disk testing method as claimed in claim 1, wherein the defect data further includes the type of defect and wherein the first magnetic disks are tested in a subsequent certifying step and a classification condition is set in the classifying step according to a result of the test in the certifying step.

9. A magnetic disk testing method as claimed in claim 1, wherein the defect data further includes the type of defect and wherein a subsequent certifying test step is performed on the first magnetic disk sampled, on the defect position of the first magnetic disk and an area in the vicinity of the defect position thereof or on a track of said first magnetic disk with a pitch of the track being roughed.

10. A magnetic disk testing device for optically testing defects of a magnetic disk, comprising:

detection means for detecting the size of surface defects of the magnetic disk, the continuity thereof, the number thereof and the position thereof as a defect data; and classification means for classifying the magnetic disks having the surface defects thus tested in said optical magnetic disk test to first magnetic disks, second magnetic disks and third magnetic disks on the basis of the defect data obtained by said detection means, said first magnetic disks being to be qualified in a subsequent test device, said second magnetic disks including magnetic disks to be decided as qualified in said subsequent test device, said third magnetic disks being to be certainly disqualified in said subsequent test device.

11. A magnetic disk testing device as claimed in claim 10, wherein the defect data further includes the type of defect and said subsequent test device comprises a glide tester and a certifier for certifying an electric characteristics of the magnetic disk, said certifier certifying magnetic disks of said second magnetic disks, which are qualified in said glide tester.

12. A magnetic disk testing device as claimed in claim 11, further comprising defect data output means for providing at least the defect position data of said second magnetic disks and an identification information for distinguishing said second magnetic disks from other magnetic disks as a defect information.

13. A magnetic disk testing device as claimed in claim 12, wherein the defect information is read by said glide tester and performs a glide test in a position of surface defect of said second magnetic disk, an area in the vicinity of the position, a sector of said second magnetic disk including the position of defect or a track of said second magnetic disk including the position of defect according to the defect position data obtained from the defect position data.

14. A magnetic disk testing device as claimed in claim 13, wherein said glide tester newly outputs at least the defect position data and an identification information for distinguishing said second magnetic disks from the other magnetic disks as a defect information correspondingly to said second magnetic disks tested by said glide tester and said certifier performs a certifying test in a position of surface defect of said second magnetic disk, an area in the vicinity of the position, a sector of said second magnetic disk including the position of defect or a track of said second magnetic disk including the position of defect according to a new defect position data obtained from the new defect information.

15. A magnetic disk testing device as claimed in claim 11, wherein the type of defect includes defect with which a data read/write with respect to a magnetic disk related thereto is substantially impossible and said classification means extracts said first magnetic disks from said magnetic disks to be tested, extracts said third magnetic disks from said magnetic disks said first magnetic disks of which are removed, classifies the remaining magnetic disks to said second magnetic disk, said classification means references said defect with which a data read/write with respect to a magnetic disk related thereto is substantially impossible when said classification means extracts said third magnetic disks.

16. A magnetic disk testing device as claimed in claim 10, wherein the defect data further includes the type of defect and said certifier performed the certifying test on said first magnetic disk and a classification condition in said classification means is set according to a result of the certifying test.

17. A magnetic disk testing device as claimed in claim 10, wherein the defect data further includes the type of defect and the certifying test step is performed on the first magnetic disk sampled, on the defect position of the first magnetic disk and an area in the vicinity of the defect position thereof or on a track of said first magnetic disk with a pitch of the track being roughed.

* * * * *